US010156520B2

(12) United States Patent
Lewis

(10) Patent No.: US 10,156,520 B2
(45) Date of Patent: Dec. 18, 2018

(54) ARRAY BASED SAMPLE CHARACTERIZATION

(71) Applicant: Malvern Instruments Limited, Worcestershire (GB)

(72) Inventor: E. Neil Lewis, Columbia, MD (US)

(73) Assignee: MALVERN PANALYTICAL LIMITED, Malvern, Worcestershire (GB)

( * ) Notice: Subject to any disclaimer, the term of this patent is extended or adjusted under 35 U.S.C. 154(b) by 0 days.

(21) Appl. No.: 14/787,953

(22) PCT Filed: Jun. 6, 2014

(86) PCT No.: PCT/IB2014/062017
§ 371 (c)(1),
(2) Date: Oct. 29, 2015

(87) PCT Pub. No.: WO2014/195917
PCT Pub. Date: Dec. 11, 2014

(65) Prior Publication Data
US 2016/0252453 A1 Sep. 1, 2016

Related U.S. Application Data

(60) Provisional application No. 61/834,330, filed on Jun. 12, 2013, provisional application No. 61/832,699, filed on Jun. 7, 2013.

(51) Int. Cl.
*G01J 5/00* (2006.01)
*G01N 21/53* (2006.01)
(Continued)

(52) U.S. Cl.
CPC ......... *G01N 21/53* (2013.01); *G01N 15/1463* (2013.01); *G01N 21/05* (2013.01);
(Continued)

(58) Field of Classification Search
CPC .... G01N 21/35; G01N 2201/10; G01N 21/31; G01N 21/33; G01N 2201/068;
(Continued)

(56) References Cited

U.S. PATENT DOCUMENTS 4,360,270 A * 11/1982 Jeck .................... G01N 21/4785
356/243.1
4,396,528 A * 8/1983 Abbott ................. C09K 11/025
252/301.17
(Continued)

FOREIGN PATENT DOCUMENTS

| CN | 102445406 | 4/2013 |
| JP | 2003262616 | 9/2003 |
| WO | WO 2013/072806 | 5/2013 |

OTHER PUBLICATIONS

International Preliminary Report on Patentability, Written Opinion and International Search Report dated Dec. 8, 2015, directed towards International Application No. PCT/IB2014/062017, 18 pages.

(Continued)

*Primary Examiner* — Kiho Kim
(74) *Attorney, Agent, or Firm* — Morrison & Foerster LLP

(57) ABSTRACT

An optical sample characterization method is disclosed comprising: holding a sample in a sample container proximate at least one two-dimensional detector array assembly, wherein the sample container has a first end and a second end; setting up a gradient between the first end of the sample container and the second end of the sample container; illuminating the sample between the first end of the sample container and the second end of the sample container; and detecting light received from the illuminated sample from
(Continued)

the first end of the sample container to the second end of the sample container by the two-dimensional array assembly.

16 Claims, 16 Drawing Sheets

(51) Int. Cl.
    *G01N 21/41*      (2006.01)
    *G01N 21/05*      (2006.01)
    *G01N 21/33*      (2006.01)
    *G01N 21/64*      (2006.01)
    *G01N 15/14*      (2006.01)

(52) U.S. Cl.
    CPC ............ *G01N 21/33* (2013.01); *G01N 21/41* (2013.01); *G01N 21/4133* (2013.01); *G01N 21/6452* (2013.01); *G01N 21/6454* (2013.01); *G01N 21/6458* (2013.01); *G01N 2201/068* (2013.01); *G01N 2201/0636* (2013.01); *G01N 2201/06113* (2013.01); *G01N 2201/12* (2013.01)

(58) Field of Classification Search
    CPC ............ G01N 21/05; G01N 2201/061; G01N 21/3563; G01N 21/3577; G01N 21/41; G01N 21/53; G01N 2201/0633; G01N 2201/0636; G01N 2201/12
    USPC ...................................... 250/338.1
    See application file for complete search history.

(56) References Cited

U.S. PATENT DOCUMENTS

| | | | |
|---|---|---|---|
| 4,681,437 A | | 7/1987 | Owen et al. |
| 4,685,328 A | * | 8/1987 | Huebner ............... G01N 11/06 73/295 |
| 4,842,406 A | * | 6/1989 | VonBargen ........ G01N 15/0205 356/336 |
| 4,999,513 A | * | 3/1991 | Ito ........................ G01N 15/147 250/575 |
| 5,395,502 A | | 3/1995 | Pawliszyn |
| 5,835,211 A | * | 11/1998 | Wells ................. G01N 15/0205 356/335 |
| 5,905,568 A | | 5/1999 | McDowell et al. |
| 6,122,042 A | * | 9/2000 | Wunderman ............ A61B 1/05 356/343 |
| 6,509,192 B1 | * | 1/2003 | Young ................ G01N 15/1012 436/10 |
| 7,187,443 B1 | * | 3/2007 | Synowicki ........... G01N 21/211 356/369 |
| 2001/0006416 A1 | | 7/2001 | Johnson |
| 2002/0135750 A1 | * | 9/2002 | Arndt ........................ G01P 5/20 356/28.5 |
| 2002/0143437 A1 | * | 10/2002 | Handique ........... B01F 13/0071 700/266 |
| 2002/0168046 A1 | * | 11/2002 | Hansen ................. G01N 23/06 378/51 |
| 2003/0235924 A1 | | 12/2003 | Adams et al. |
| 2004/0001618 A1 | | 1/2004 | Johnson et al. |
| 2005/0037499 A1 | * | 2/2005 | Ramberg ........... G01N 21/4738 436/3 |
| 2005/0185188 A1 | * | 8/2005 | McGrew ................ B82Y 10/00 356/450 |
| 2005/0237525 A1 | * | 10/2005 | Wu ..................... G01N 15/1475 356/338 |
| 2007/0086918 A1 | * | 4/2007 | Hartley .............. G01N 15/1484 422/73 |
| 2007/0155017 A1 | * | 7/2007 | Wyatt ................ G01N 15/0255 436/45 |
| 2008/0190220 A1 | * | 8/2008 | Backes ................. B29C 66/542 73/864.81 |
| 2008/0291456 A1 | * | 11/2008 | Ghislain .............. G01N 29/022 356/450 |
| 2009/0152475 A1 | * | 6/2009 | Sasaki ........................ G01J 3/10 250/492.1 |
| 2009/0184247 A1 | * | 7/2009 | Shimazu ............ G01N 21/3563 250/339.11 |
| 2010/0097599 A1 | | 4/2010 | Lewis et al. |
| 2010/0225898 A1 | | 9/2010 | Lenke et al. |
| 2010/0225913 A1 | * | 9/2010 | Trainer .............. G01N 15/0205 356/338 |
| 2010/0296094 A1 | | 11/2010 | Yang et al. |
| 2010/0309457 A1 | | 12/2010 | Cui et al. |
| 2011/0001967 A1 | * | 1/2011 | Utsunomiya ........ G01N 21/553 356/319 |
| 2011/0170105 A1 | | 7/2011 | Cui et al. |
| 2012/0044493 A1 | * | 2/2012 | Smart ................. G01N 15/0211 356/336 |
| 2012/0061587 A1 | | 3/2012 | Wu et al. |
| 2012/0126142 A1 | | 5/2012 | Matsui et al. |
| 2012/0199742 A1 | * | 8/2012 | Wagner ................ C12N 5/0612 250/338.1 |
| 2012/0224053 A1 | | 9/2012 | Vykoukal et al. |
| 2012/0228519 A1 | * | 9/2012 | Gilmore ............... G01N 21/645 250/459.1 |
| 2012/0301967 A1 | * | 11/2012 | Nadkarni ........... G01N 33/4905 436/69 |
| 2013/0010294 A1 | * | 1/2013 | Matsuda ............ G01N 21/3563 356/326 |
| 2013/0265566 A1 | * | 10/2013 | Smith ........................ G01J 3/10 356/39 |
| 2013/0301051 A1 | * | 11/2013 | Pogosyan .............. G01J 1/0411 356/432 |
| 2014/0177932 A1 | * | 6/2014 | Milne .................... G06T 7/0012 382/128 |
| 2014/0230527 A1 | * | 8/2014 | Lewis .................... G01N 11/06 73/54.06 |
| 2014/0232853 A1 | | 8/2014 | Lewis |

OTHER PUBLICATIONS

Cui, Xiquan et al., "Lensless high-resolution on-chip optofluidic microscopes for Caenorhabditis elegans and cell imaging," (2008) Proceedings of the National Academy of Sciences, vol. 105, No. 31, pp. 10670-10675.

Ozcan, Aydogan et al., "Ultra wide-field lens-free monitoring of cells on-chip," (2008) The Royal Society of Chemistry, Lab Chip, vol. 8, No. 1, pp. 98-106.

European Patent Office examination report dated Jul. 3, 2017, directed to European Application No. 14 731 821.6; 17 pages.

\* cited by examiner

Line or multi-point laser excitation

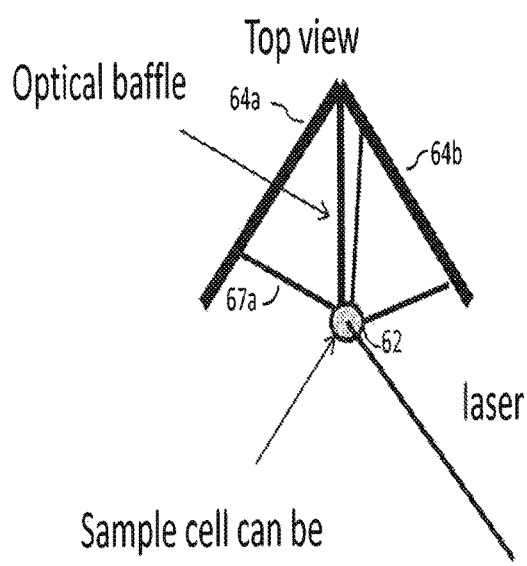
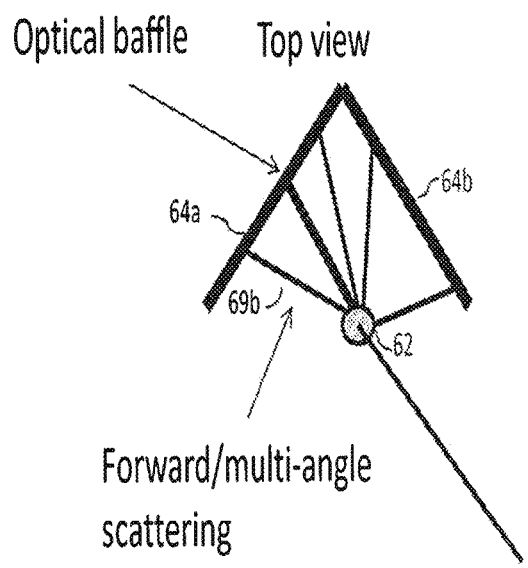
FIG. 6b
FIG. 6c

Malvern APS micro-titer plate platform or Prince carousel unit. Could also be sip directly from 'pre-filled' vials.

ARRAY BASED SAMPLE CHARACTERIZATION

CROSS-REFERENCE TO RELATED APPLICATIONS

This application is a national phase filing under 35 U.S.C. § 371 of International Application No. PCT/IB2014/062017, filed Jun. 6, 2014, and which claims priority to U.S. Provisional Patent Application Nos. 61/834,330, filed Jun. 12, 2013, and 61/832,699, filed Jun. 7, 2013, the contents of which are incorporated herein by reference.

FIELD OF THE INVENTION

This invention relates to methods and apparatus for detecting properties of samples, such as liquid samples, solid samples, solutions, slurries, and suspensions.

BACKGROUND OF THE INVENTION

Lensless microfluidic detection techniques have been proposed to acquire microscopic images of samples such as biological materials and cells. They operate by acquiring images of suspended samples in close proximity to a high-resolution imaging detector. Their small size has resulted in their use being proposed in a variety of life science applications, including microscopes, smart petri dishes, and point-of-care diagnostic systems.

SUMMARY OF THE INVENTION

A number of embodiments are presented in connection with the description, drawings, and claims of this application.

Systems according to the invention can help to inexpensively characterize small samples of a variety of different materials in different ways. These systems are applicable in research and industrial settings, such as in the development and manufacture of pharmaceuticals, personal care products, foodstuffs, pigments, and biomaterials, as well as in the areas of Metals, Mining, and Minerals (MMM). Their versatility and/or ability to characterize small samples can help to quickly develop materials and provide ongoing quality control and quality assurance in their handling and manufacture.

BRIEF DESCRIPTION OF THE DRAWING

FIG. 6b is a diagrammatic top view of the system of FIG. 6a showing a first baffle position, FIG. 6c is a diagrammatic top view of the system of FIG. 6a showing a second baffle position.

DETAILED DESCRIPTION OF AN ILLUSTRATIVE EMBODIMENT

Figure 1:
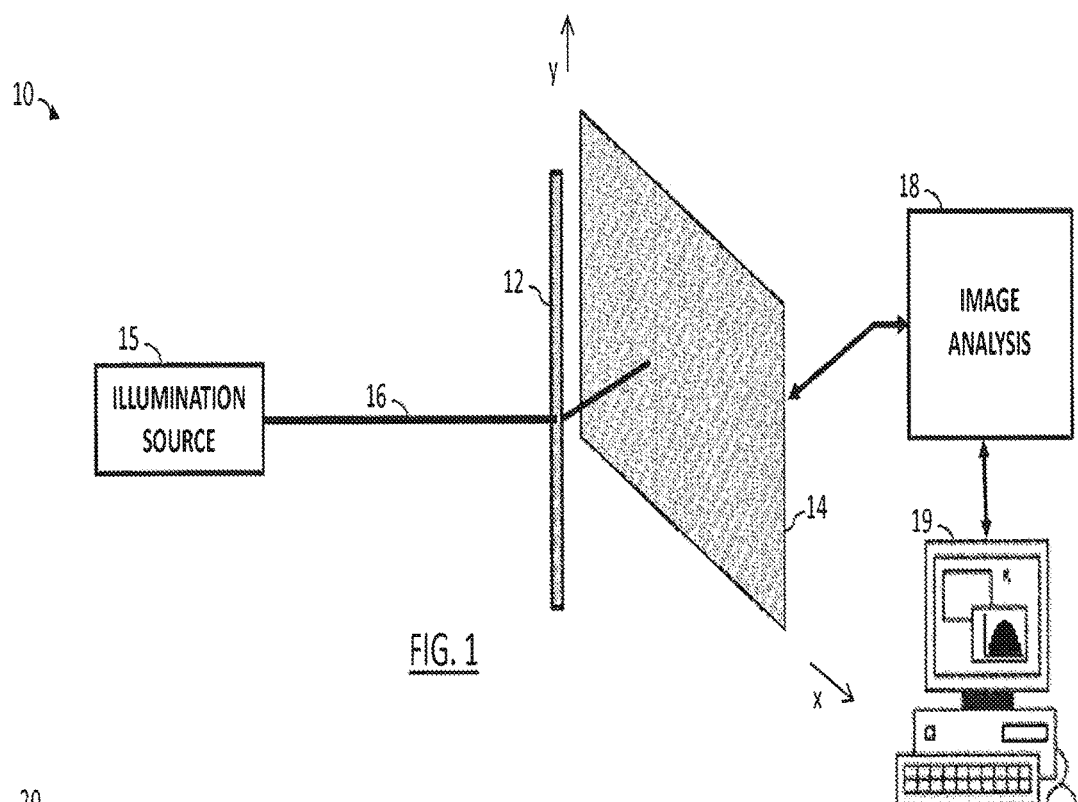
FIG. 1 is a diagrammatic perspective view of a sample characterization system according to the invention that measures a refractive index of a sample.

Referring to FIG. 1. a sample characterization system 10 according to the invention characterizes a sample held in sample holder 12. It includes an illumination source 15, such as a laser positioned to shine its output radiation 16 toward the sample holder. A two-dimensional array detector 14 is positioned at least generally opposite the test vessel from the laser. Image analysis logic 18 is operatively connected to a data output of the two-dimensional array detector. This logic can be connected to and/or implemented using a computer 19.

The two-dimensional array detector 14 can be any suitable type of array, such as such as a CCD or CMOS array detector. It can be a relatively high resolution array, such as one having a pixel pitch of under around 10 microns. In one embodiment, the array is implemented using a Sony 8MP smartphone camera chip. The color separation filters have been removed in this embodiment, but they can be used in other embodiments to detect light of different wavelengths.

Spectral filters can also be provided between the illumination source and the two-dimensional array detector, such as by depositing them on the array detector chip or as a separate element. These filters allow the system designer to filter out noise and/or focus on one or more wavelengths of interest. As is well known, these filters can be low-pass, high-pass, or band-pass filters, or combinations thereof. Linear variable filters can also be used in some embodiments to acquire measurements at several wavelengths.

The sample holder can hold a sample in a number of different ways. For a liquid sample, the holder can be implemented as a cuvette, a capillary tube, a flow cell, a droplet holder or other suitable holder for a liquid sample. In one embodiment, the liquid sample holder is a square capillary tube. The liquid sample can include one of a variety of types of liquids, such as solutions, slurries, dispersions, or suspensions.

The sample holder can also be configured to hold a solid sample, such as a crystal or a powder. This type of holder can be implemented in a variety of different ways, such as a platform, clamp, or powder vial. Gaseous samples can also be accommodated, such as in sealed vials.

The image analysis logic 18 can be implemented using special-purpose hardware, such as a dedicated image processing card and/or with one or more special-purpose software programs running on one or more general-purpose computer platforms 19. The computer can also control other functions of the instrument, such as turning the illumination source on and off and/or controlling the array detector. Although not shown in the remaining drawings for the sake of clarity these types of parts can be provided for each of the embodiments presented in the application. Similarly, although not shown in all of the remaining drawings for the sake of clarity, illumination sources are used to produce beams shown in connection with the different embodiments.

In operation, the illumination source 15 illuminates the sample in the sample holder 12 with a sample output beam 16. The sample then refracts the beam by an amount related to its refractive index. This causes a resulting refracted beam to land at a position on the array along one or more of the axes that corresponds to the sample's refractive index. The image analysis logic 18 can then calculate a value of the refractive index, such as by counting pixels and/or interpolating subpixels in one or more directions. Note that while the drawings show the x-direction as being horizontal, this and other embodiments can be constructed to detect deflection in other directions.

Figure 2:
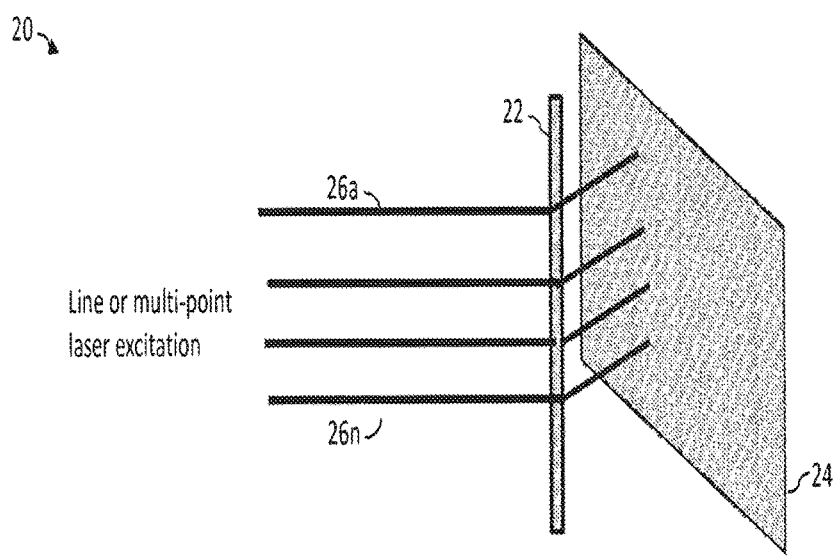
FIG. 2 is a diagrammatic perspective view of a sample characterization system according to the invention that measures a refractive index of multiple parts of a sample.

Referring to FIG. 2, another embodiment of a sample characterization system 20 according to the invention characterizes a sample held in sample holder 12 at multiple places along the sample holder. It includes a plurality of illumination sources, such as lasers, positioned to shine their output beams 26a . . . 26n toward the .sample holder. A two-dimensional array detector 24 is positioned at least generally opposite the test vessel from the lasers.

This embodiment differs from that shown in FIG. 1 in that the sample is illuminated at multiple different points along its length (y-axis). This allows readings for multiple sample points to be detected simultaneously. This type of embodiment can allow measurements at different places on non-uniform samples, such as where a gradient exists in the fluid or where the fluid is flowing through the sample holder, such as from a liquid chromatography column. It may also allow averaging to take place to reduce the effect of unintended or undesirable heterogeneity in the sample.

Figure 3:
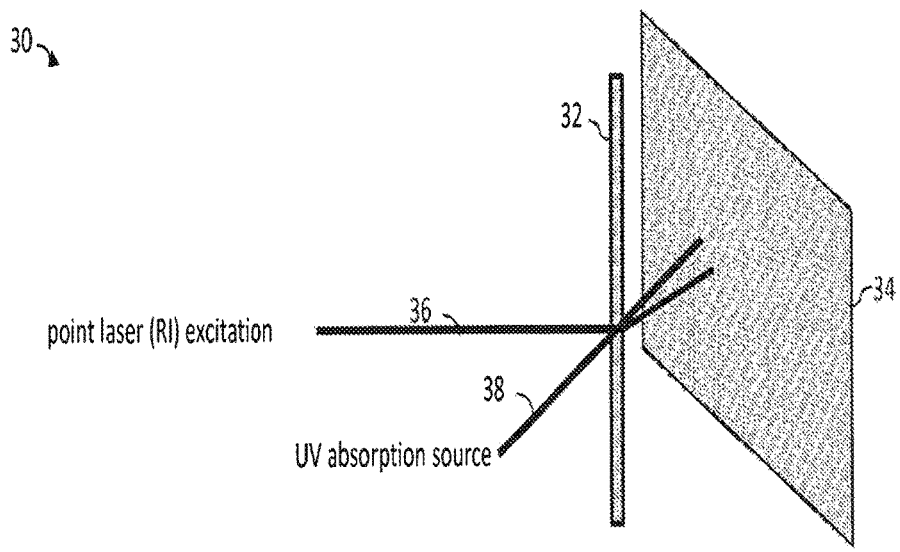
FIG. 3 is a diagrammatic perspective view of a sample characterization system according to the invention that measures both the a refractive index and UV absorption of a sample.

Referring to FIG. 3, a further embodiment of a sample characterization system 30 according to the invention characterizes a sample held in sample holder 32. It includes a first illumination source, such as a laser positioned to shine its output radiation 36 toward the sample holder, and second illumination source, such as an ultraviolet absorption source positioned to shine its output radiation 38 toward the sample holder. A two-dimensional array detector 34 is positioned at least generally opposite the test vessel from the laser. Image analysis logic is operatively connected to a data output of the two-dimensional array detector.

In operation, the illumination source illuminates the sample in the sample holder 32 with a first sample output beam 36. The sample then causes the beam to refract by an amount related to its refractive index. This causes a resulting refracted beam to land at a position on the array along the x-axis that corresponds to the refractive index. The image analysis logic 38 can then calculate the refractive index, such as by counting pixels and/or interpolating subpixels in the x-direction, The system can also illuminate the sample with a second sample output beam 38. This beam is positioned to provide a transmission measurement, such as a UV transmission measurement. The intensity of the beam received at the detector will therefore be indicative of the degree of absorption by the sample for the beam. Using filters, this measurement can be restricted to one or more spectral regions of interest.

The two types of measurements are performed during alternating periods in the present embodiment. It may be possible, however, to perform the measurements simultaneously in some circumstances.

Figure 4:
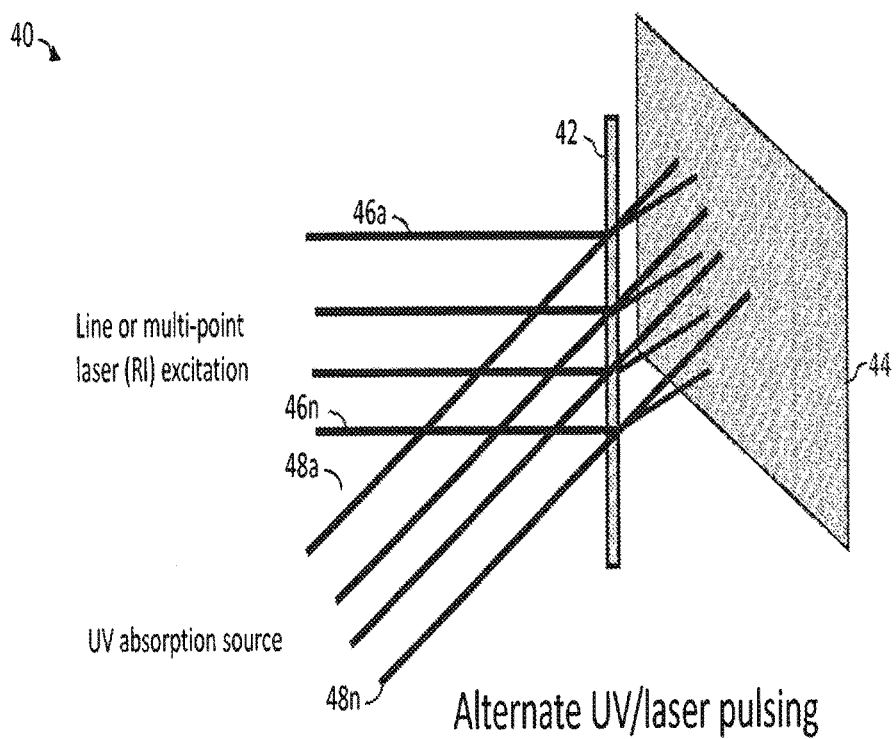
FIG. 4 is a diagrammatic perspective view of a sample characterization system according to the invention that measures both the a refractive index and UV absorption of multiple parts of a sample.

Referring to FIG. 4, another embodiment of a sample characterization system 40 according to the invention characterizes a sample held in sample holder 32 at multiple places along the sample holder. It includes a plurality of first illumination sources, such as lasers positioned to shine their output radiation beams 46a . . . 46n toward the sample holder. It also includes a plurality of second illumination sources, such as ultraviolet absorption sources positioned to shine their output radiation beams 48 toward the sample holder. A two-dimensional array detector 44 is positioned at least generally opposite the test vessel from the laser. This embodiment differs from that shown in FIG. 3 in that sample is illuminated at multiple points different points along its length (y-axis). This allows two readings each for multiple sample points to be detected simultaneously.

Figure 5A:
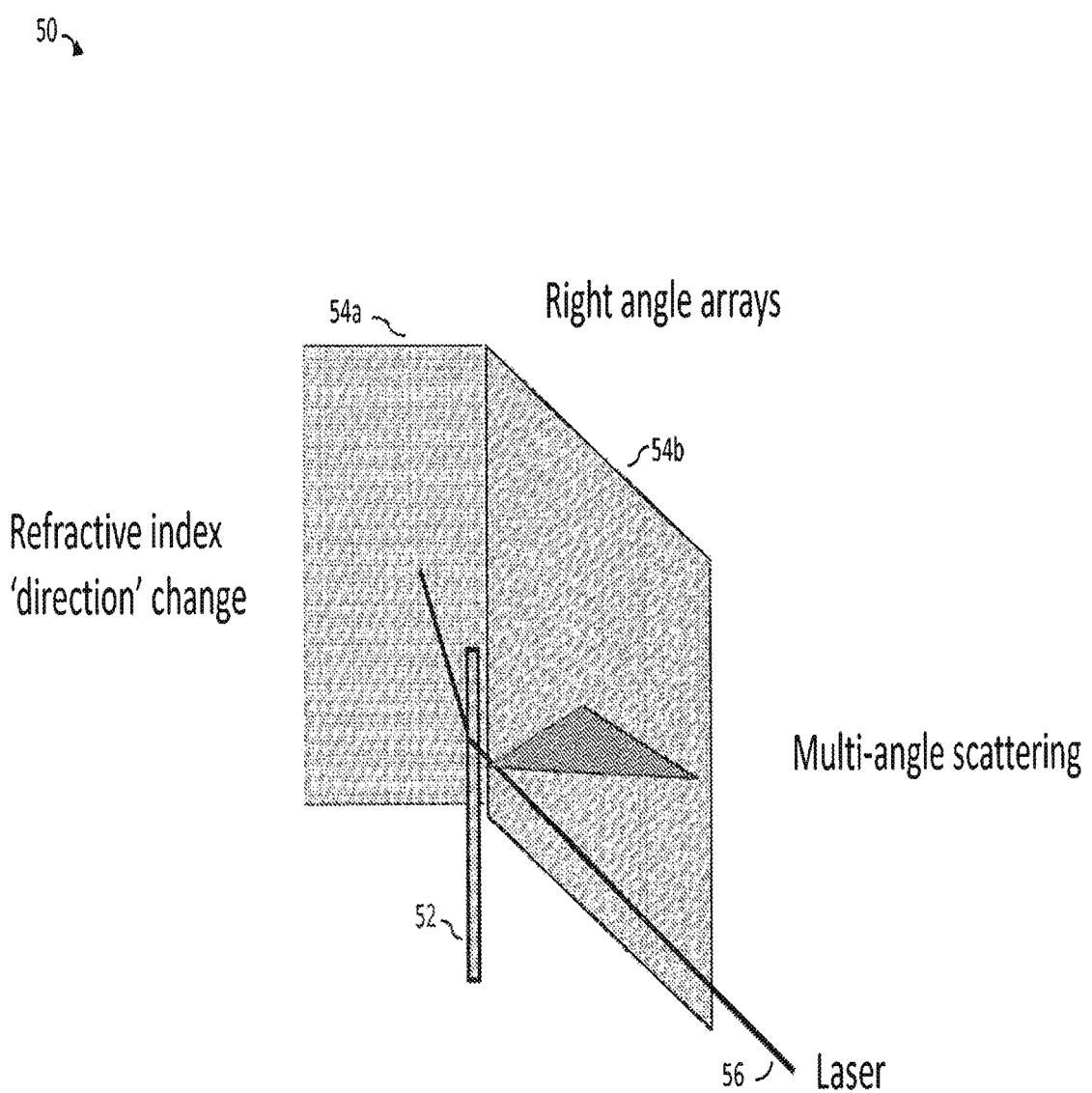
FIG. 5a is a diagrammatic perspective view of a sample characterization system according to the invention that measures both the a refractive index and multi-angle scattering characteristics of a sample.

Referring to FIG. 5a, a further embodiment of a sample characterization system 50 according to the invention characterizes a sample held in sample holder 52 using two or more two-dimensional array detectors 54a, 54b. In this embodiment, the arrays are identical and are placed at right angles with respect to each along an upright edge, although other angles, orientations, and numbers of arrays can also be used, and different types of arrays can be mixed, such as arrays with different numbers of pixels, different pixel densities, or different spectral sensitivities. In the present embodiment, the arrays form two sides of an incomplete cube, with the sample holder being placed generally in the center of the cube, but other configurations are also possible. A beam 56 from an illumination source such as a laser is directed towards the sample holder, such as through an open side of the cube.

Figure 5B:
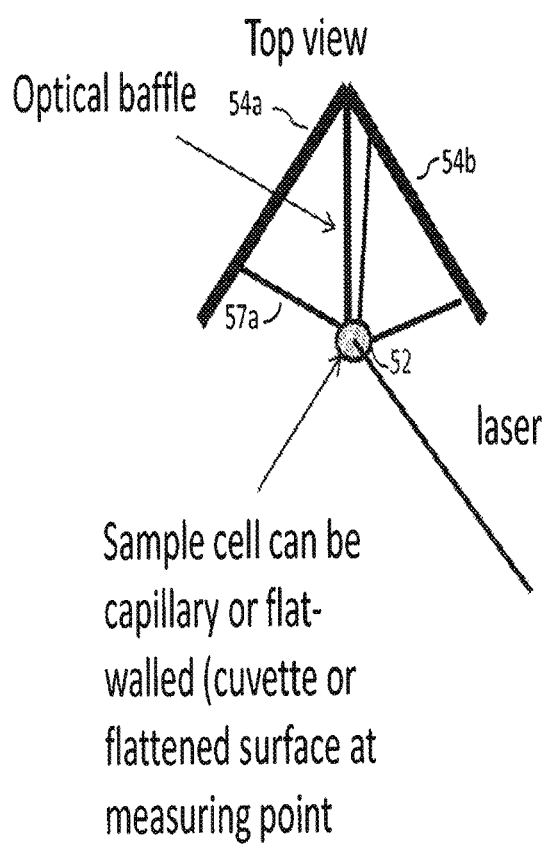
FIG. 5b is a diagrammatic top view of the system of FIG. 5a showing a first baffle position.

In operation, the illumination source illuminates the sample in the sample holder 52 with an output beam 56. In the case of a liquid sample, the sample can then cause the beam to scatter in a manner that is related to the molecular weight of solutes and/or suspended particles in the sample. This generally causes scattered light to reach different parts of the array, with larger molecular weights scattering less uniformly, Image analysis logic can then calculate an effective molecular weight for the sample, such as by summing scattered light intensity from different angles detected at different locations and comparing the result to an incident beam intensity. Referring to FIGS. 5a and 5b, optical baffles can act as a zero-degree beam stop, or they can be used to prevent stray light, such as reflections from one measurement from affecting another.

Figure 5C:
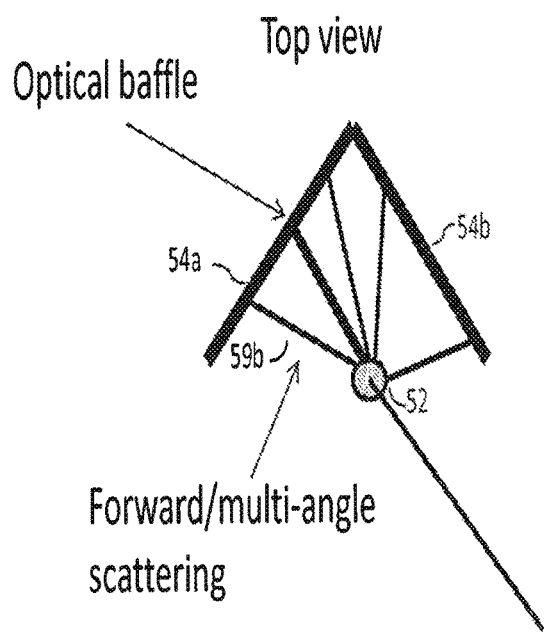
FIG. 5c is a diagrammatic top view of the system of FIG. 5a showing a second baffle position.
Figure 6A:
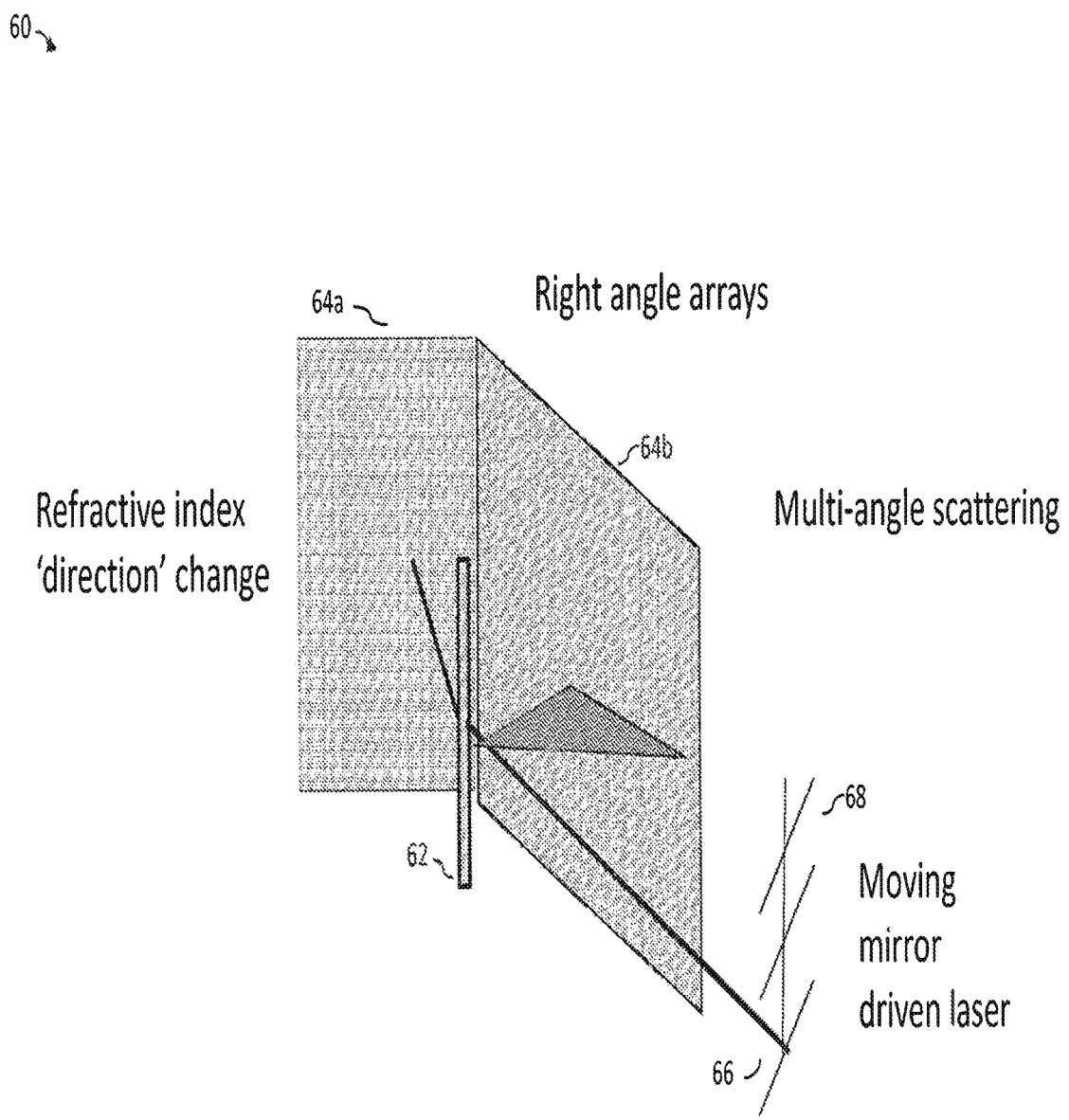
FIG. 6a is a diagrammatic perspective view of a sample characterization system according to the invention that measures both the a refractive index and multi-angle scattering characteristics of different parts of a sample.

Referring to FIGS. 6a-c, another embodiment of a sample characterization system 60 can .acquire samples from different parts of the sample holder. This embodiment differs from that of FIGS. 5a-C that it allows an illumination beam 66 to illuminate the sample at different locations.

Figure 7:
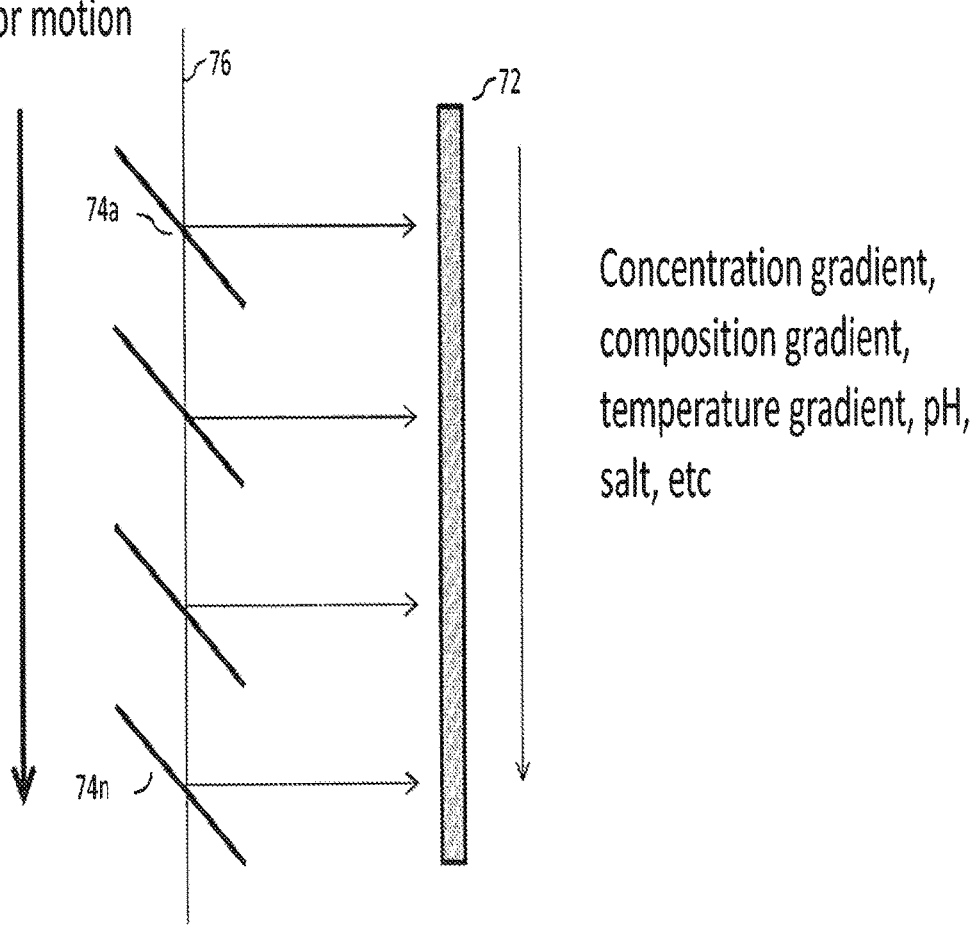
FIG. 7 is a diagrammatic elevation view of a moving mirror accessory for sample characterization system according to the invention that can excite different parts of a sample, such as different parts of a sample gradient.

Referring to FIG. 7, a plural beam generator 70 can be implemented using a movable mirror system 70, which includes a mirror that can move parallel to the length of the sample holder 72, while passing through different positions 74a . . . 74n. The mirror can thus redirect a light beam 76 to different places along the sample holder. Other methods of providing a synchronous or asynchronous plural beam generator can also be provided, such as using galvanometers or multiple sources.

Figure 8:
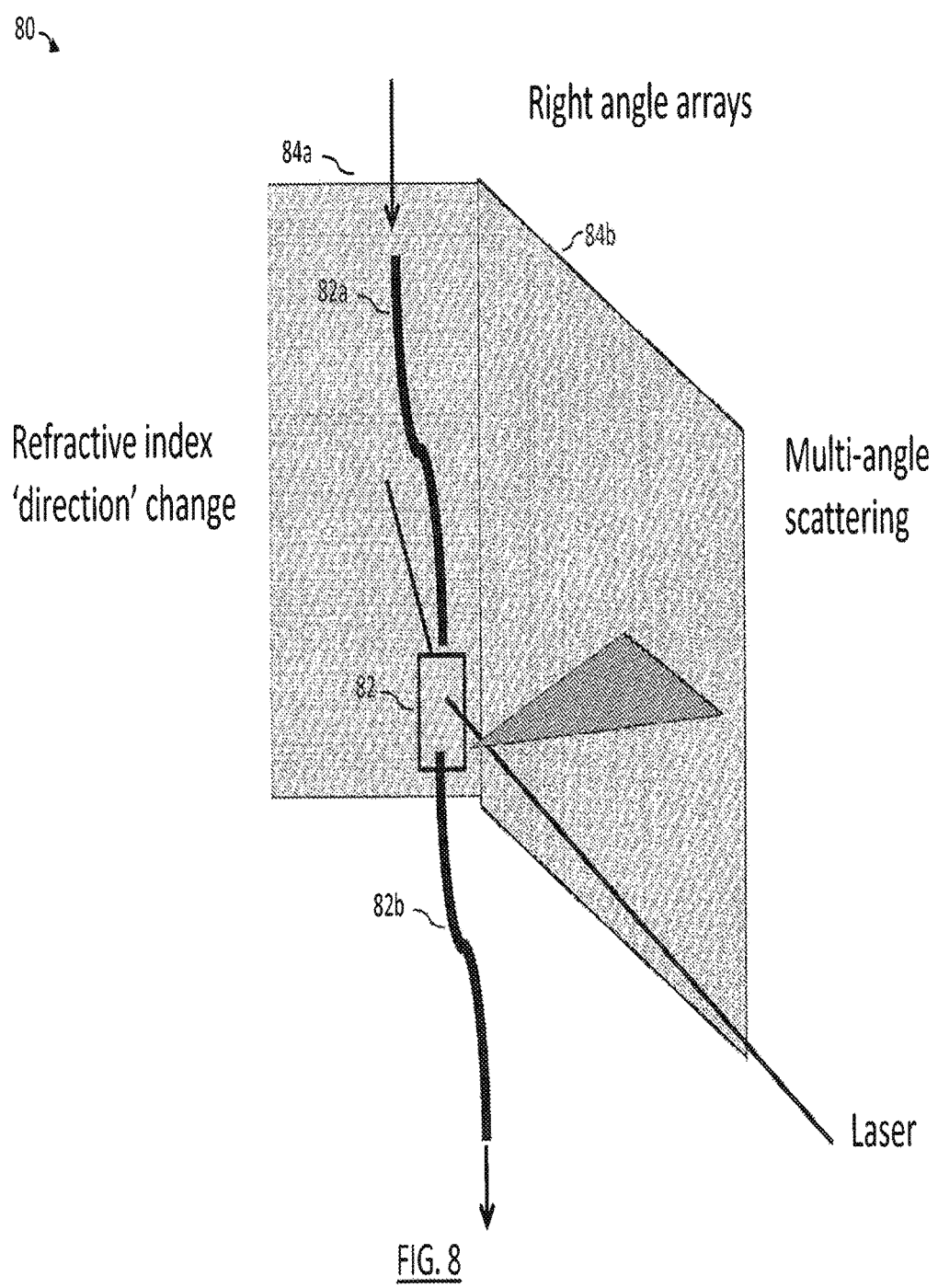
FIG. 8 is a diagrammatic perspective view of a sample characterization system according to the invention that measures both the a refractive index and multi-angle scattering characteristics of a sample flowing through a flow cell.

Referring to FIG. 8, a further embodiment of a sample characterization system 80 according to the invention includes a flow cell 82 supplied by conduits 83a, 83b. This allows measurements to be performed on flowing samples, such as the output of a liquid chromatography column, or a process feed. In this embodiment, the flow cell is shown in connection with a right-angle, laser-based multi-angle scattering setup, although it can be used in types of setups.

Figure 9A:
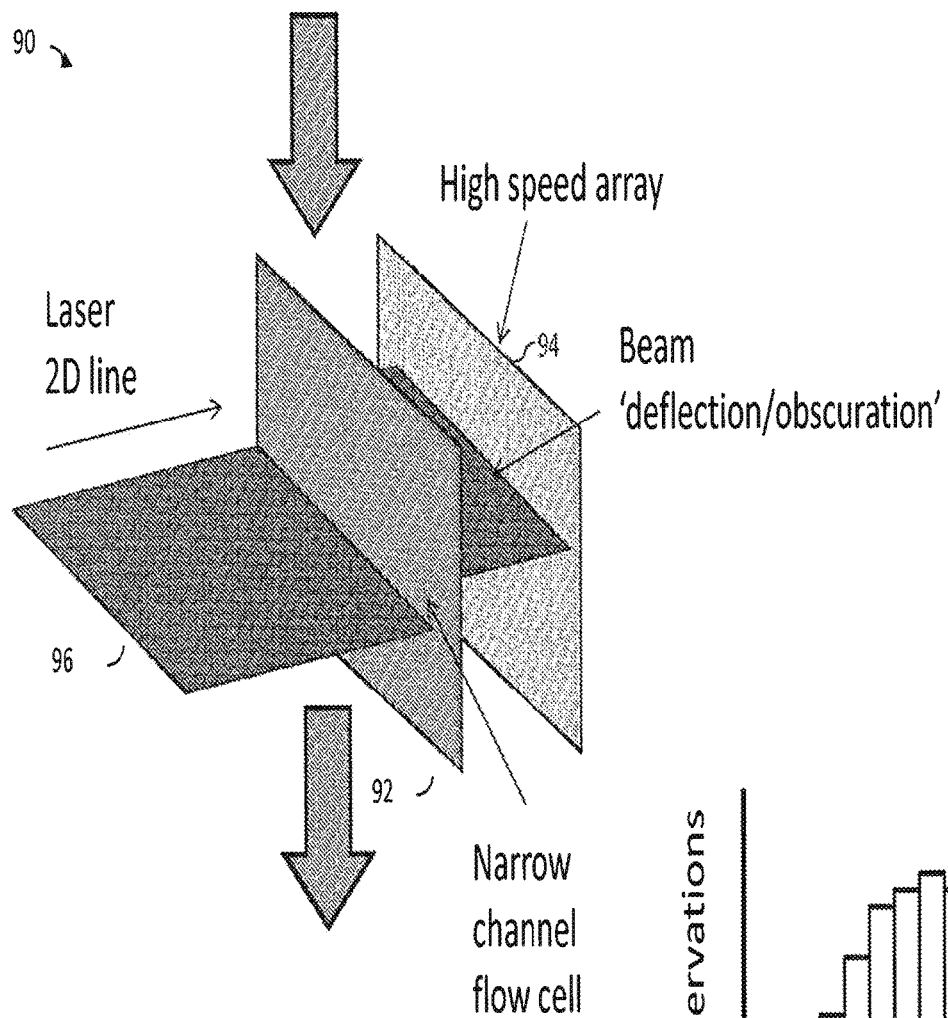
FIG. 9a is a diagrammatic perspective view of a sample characterization system according to the invention that measures both obscuration and deflection of a sample flowing through a narrow-channel flow cell.

Referring to FIG. 9, another embodiment of a sample characterization system 90 according to the invention includes a narrow-channel flow cell 92 fed with .a flowing sample. This flow cell can be placed in parallel with a two-dimensional array detector 94, which is preferably a relatively high-speed detector. A two-dimensional illumination beam 96 is then shone through the narrow-channel flow cell onto the array, preferably at least generally perpendicular to the direction of flow in the narrow-channel flow cell The illumination beam can be produced in a variety of ways, such as by shining a laser through a cylindrical lens.

Figure 9B:
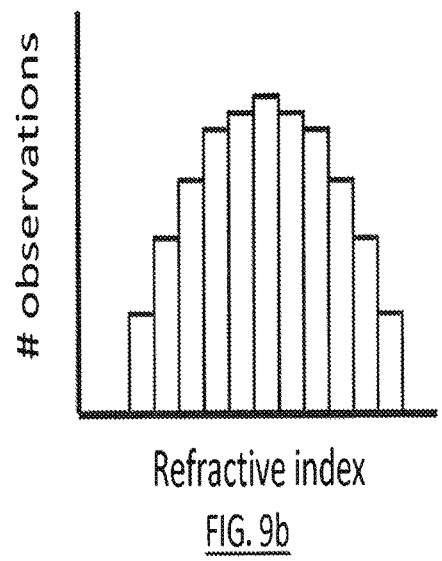
FIG. 9b is an illustrative histogram showing the frequency of observed particles for different refractive index ranges for the system of FIG. 9a, FIG. 10 is a set of five successive diagrammatic output images for the system of FIG. 9.
Figure 10:
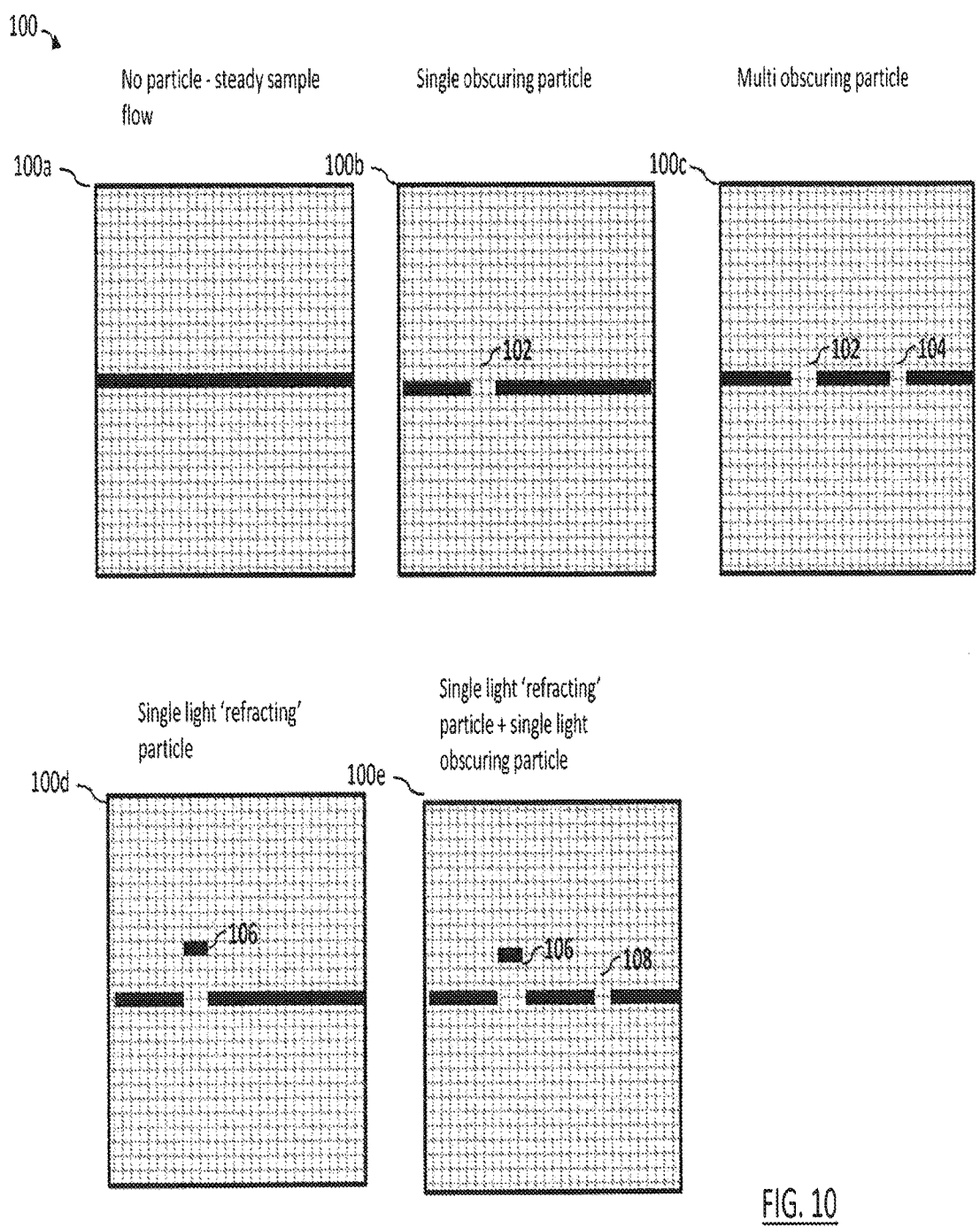

In operation, referring also to FIGS. 9B and 10, when the system is flowing with no particles present, the two-dimensional illumination beam 96 produces a line image on the array (image 100a). An opaque particle that then flows through the narrow-channel flow cell 92, will a obscure a portion of the beam 102 (image 100b). The width of the obscuration of the beam will be related to a spatial dimension of the particle. The duration of the obscuration of the beam will be related to a different spatial dimension of the particle. A second, smaller particle, for example, might therefore produce another obscuration of a portion of the beam 104, with this alteration being narrower and of shorter duration (image 100c).

A non-opaque, refracting particle refract a portion of the beam 106 by an amount related to its refractive index. This causes a resulting refracted portion of the beam to land at a position on the array that is offset along the y-axis (image 100d). The extent of deflection will be related to the refractive index of the particle, and the width of the deflection will be related to the size of the particle. Obscuring particles and refracting particles can be detected at the same time, resulting in an image with both offset 106 and obscured 108 beam portions (image 100e).

The image analysis logic can derive particle dimensions from the acquired images by converting the widths and durations associated with detected particles. The image analysis logic can also derive an index of refraction for refracting particles. These results can then be stored, statistically analyzed, or otherwise processed and displayed, such as in the form of a histogram of numbers of observed particles against their refractive indices (FIG. 9B).

Figure 11:
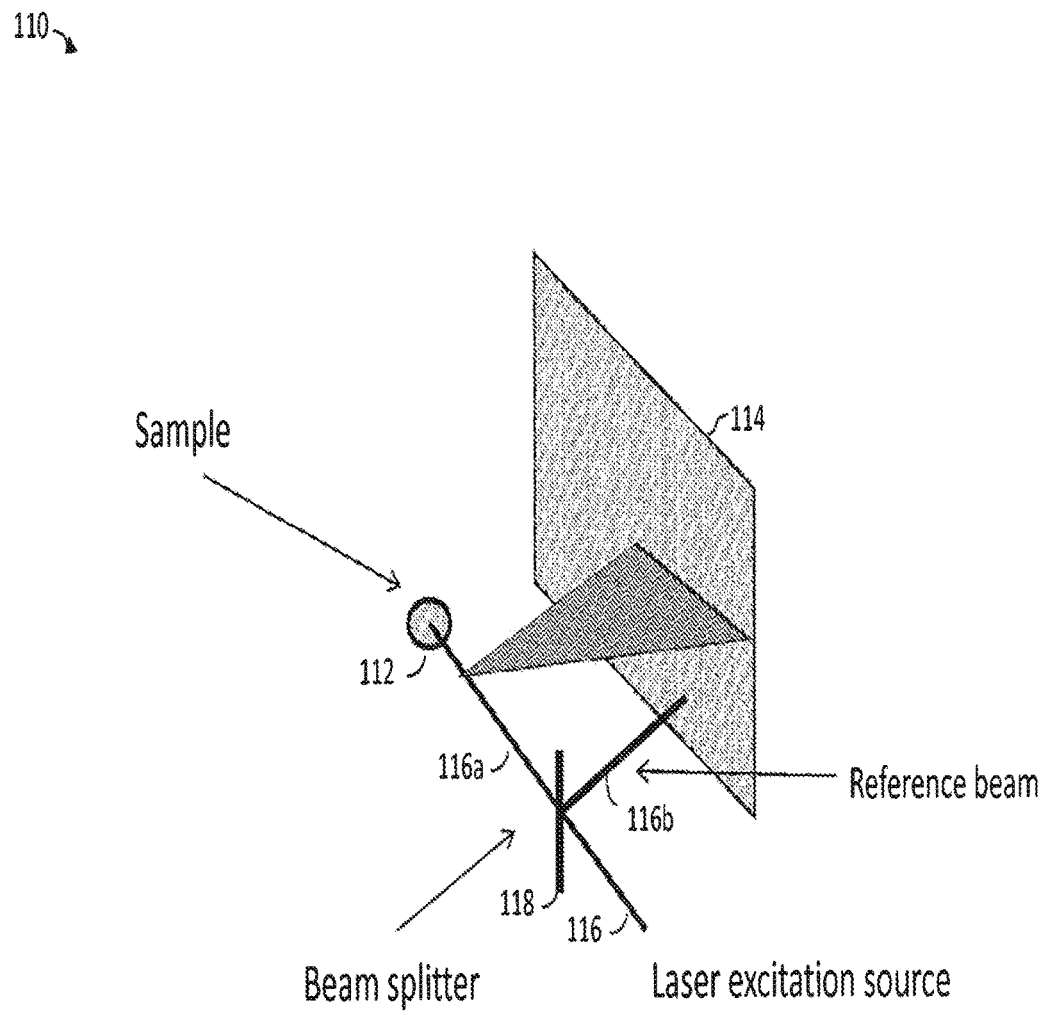
FIG. 11 is a diagrammatic perspective view of a sample characterization system according to the invention that measures multi-angle scattering using a reference beam.

Referring to FIG. 11, a further embodiment of a sample characterization system 110 according to the invention includes a reference beam extractor 118, such as a beam splitter, a bifurcated optical fiber, or an oscillating mirror. This extractor produces a reference beam in addition to the sample beam, which is used to perform one or more measurements of characteristics of a sample in a sample holder 112, such as its scattering characteristics. Both beams can then be imaged by one or more two-dimensional an-ay detectors 114.

The use of a reference beam can improve sample characteristics detection, by providing a baseline to compare measurements against. This baseline can compensate for a number of types of errors. For example, it can compensate for fluctuations or drift in the illumination source intensity, or in some embodiments it can provide information about the spectral content of the source before it is affected by interaction with the sample.

Figure 12:
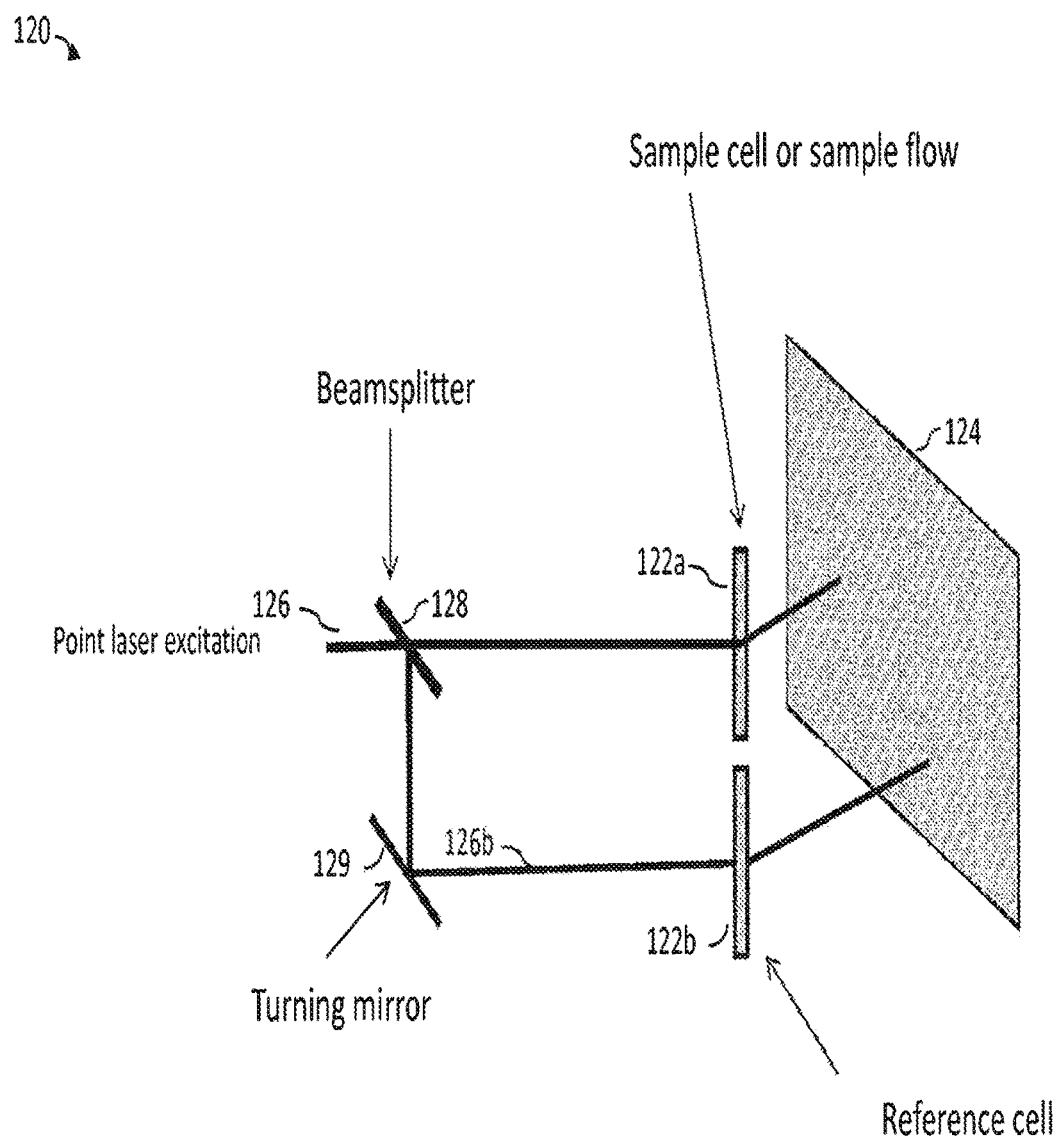
FIG. 12 is a diagrammatic perspective view of a sample characterization system according to the invention that measures a refractive index of a both a sample and a reference sample.

Referring to FIG. 12, another embodiment of a sample characterization system 110 according to the invention includes a reference beam extractor 129, such as a beam splitter, a bifurcated optical fiber, or an oscillating mirror. This extractor produces a reference beam in addition to the sample beam. The sample beam is directed through a sample holder 122a, to perform one or more measurements of characteristics of a sample, and the reference beam is directed through a reference sample holder. After interaction with the respective samples, both beams can be recorded by one or more two-dimensional array detectors 124.

The use of a reference sample can improve sample characteristics detection, by providing a baseline to compare measurements against. This baseline can compensate for a number of types of errors. Like a baseline from a sample beam, it can compensate for fluctuations or drift in the illumination source intensity, or in some embodiments it can provide information about the spectral content of the source before it is affected by interaction with the sample. It can also allow a sample to be compared against a known standard, such as a known component of the sample.

Figure 13:
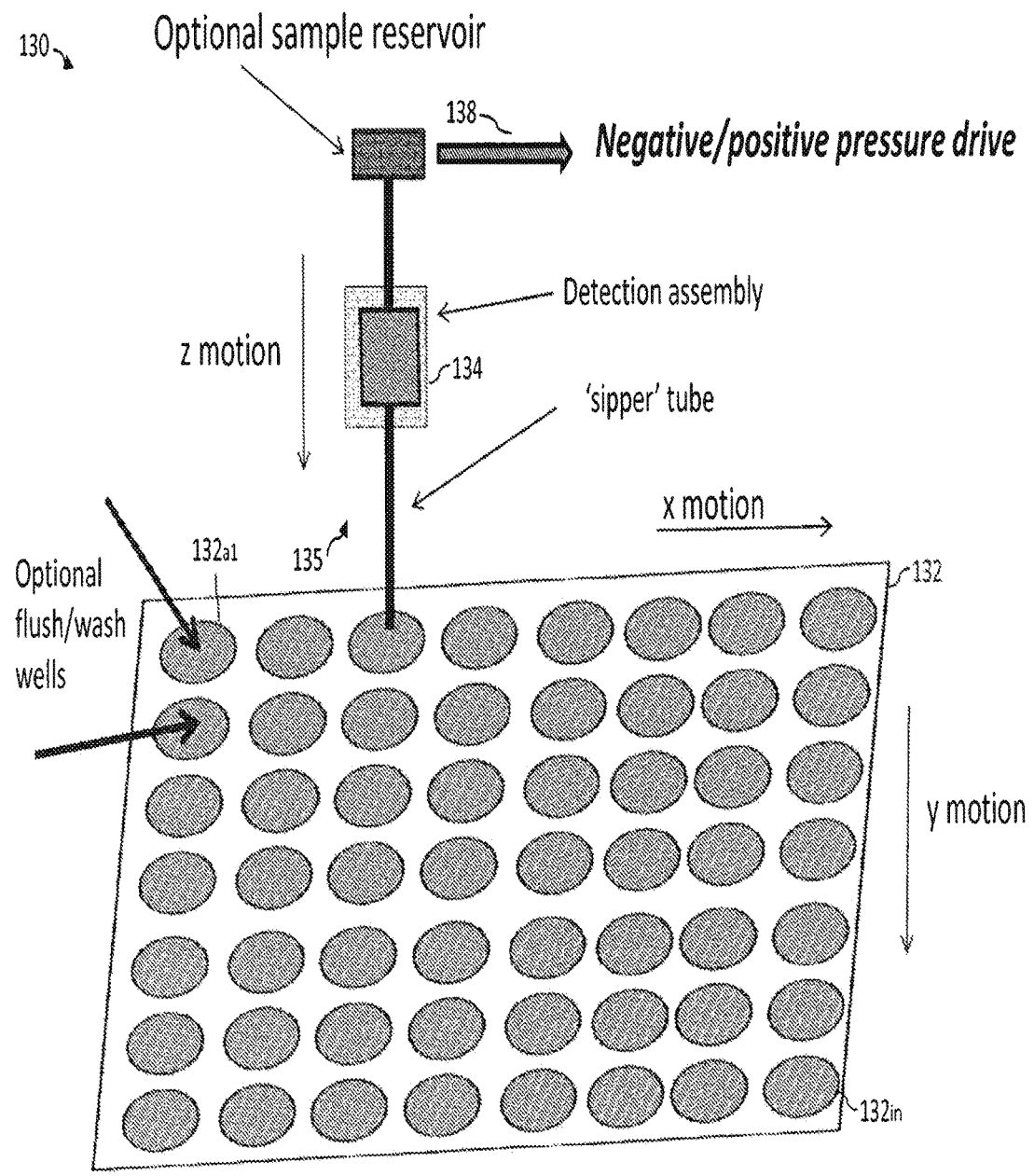
FIG. 13 is a diagrammatic block diagram of an embodiment of a high-throughput fluid characterization system according to the invention.

Referring to FIG. 13, an embodiment of a high-throughput fluid characterization system 40 according to the invention uses a probe 135 to perform successive measurements on a number of liquid samples held in different vessels, such as wells 132a1 . . . 132 in of a multi-well plate 132 or carousel. A negative/positive pressure drive 138, which can include a pump or other pressure source, is hydraulically connected to one or more capillary sipper tubes via a manifold. The capillary tubes are positioned proximate one or more two-dimensional array detectors 132 and illuminated by one or more illumination sources. The arrays and sources can be configured to perform any of the types of measurements presented in other embodiments of this application.

An off-the-shelf x-y-z stage is provided to successively position the samples under the probe, although other types of mechanisms can be used to position the vessels and probe relative to each other. Wash and waste vessels can also be provided, either in the plate, or separately.

In operation, the x-y-z stage begins by positioning a first of the wells below the probe to select a first sample. This sample is drawn into the capillary tube, which acts as the sample holder, and a measurement is performed. The sample can then returned to the vessel or discarded and the process repeated for another sample. Preferably, the process can be automated to run unattended.

Figure 14:
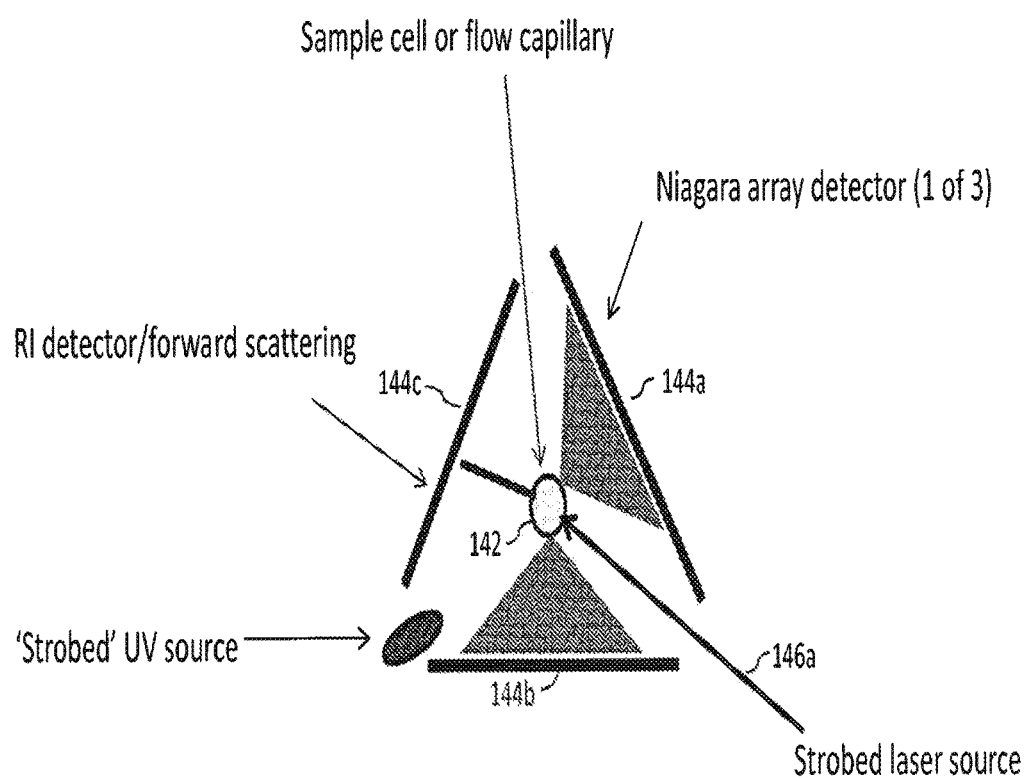
FIG. 14 is a diagrammatic top view of a three-detector sample characterization system according to the invention that measures both multi-angle scattering and UV absorption of a sample.

Referring to FIG. 14, a further embodiment of a sample characterization system 140 according to the invention includes three two-dimensional array detectors 144a, 144b, 144c, which are all oriented in the same y-direction but face inward in a spaced triangular configuration. In this case, they form an isosceles triangle with openings at each vertex. Inside the triangle is a sample holder 142 placed, in this case, at the center of mass of the triangle.

A first illumination source, such as a laser, provides a first beam 146a that is directed through the opening between the first two-dimensional array detector 144a and the second two-dimensional array detector 144b, toward the sample holder 142. A second illumination source, such as a UV source, provides a second beam that is directed through the opening between the second two-dimensional array detector 144b and the third two-dimensional array detector 1 44c, toward the sample holder. The two sources are switched or strobed such that they interact separately with the sample in the sample holder during successive sampling intervals, although it may also be possible in some embodiments to perform simultaneous measurements.

In operation, the first source excites the sample, and the resulting scattering is detected by one or more of the three two-dimensional array detectors 144a, 144b, 144c. More specifically, the third two-dimensional array detector 144c detects unscattered and low-angle forward-scattered radiation, and the first and second two-dimensional array detectors detect 90° and other high angle scattered radiation. The detected scattered radiation can then be analyzed by analysis logic. The sample can also refract the beam from the first source and the resulting deflection can be detected by the first two-dimensional detector 144a. The second source illuminates the sample with UV radiation, and radiation that is not absorbed by the sample is transmitted to and detected by the first two-dimensional array detector 144a.

While this embodiment is shown with three two-dimensional detector arrays configured in a spaced isosceles triangle with a centered sample holder in the middle, other numbers of arrays, arrangements of arrays, arrays orientations, and sample positions are also possible.

Figure 15:
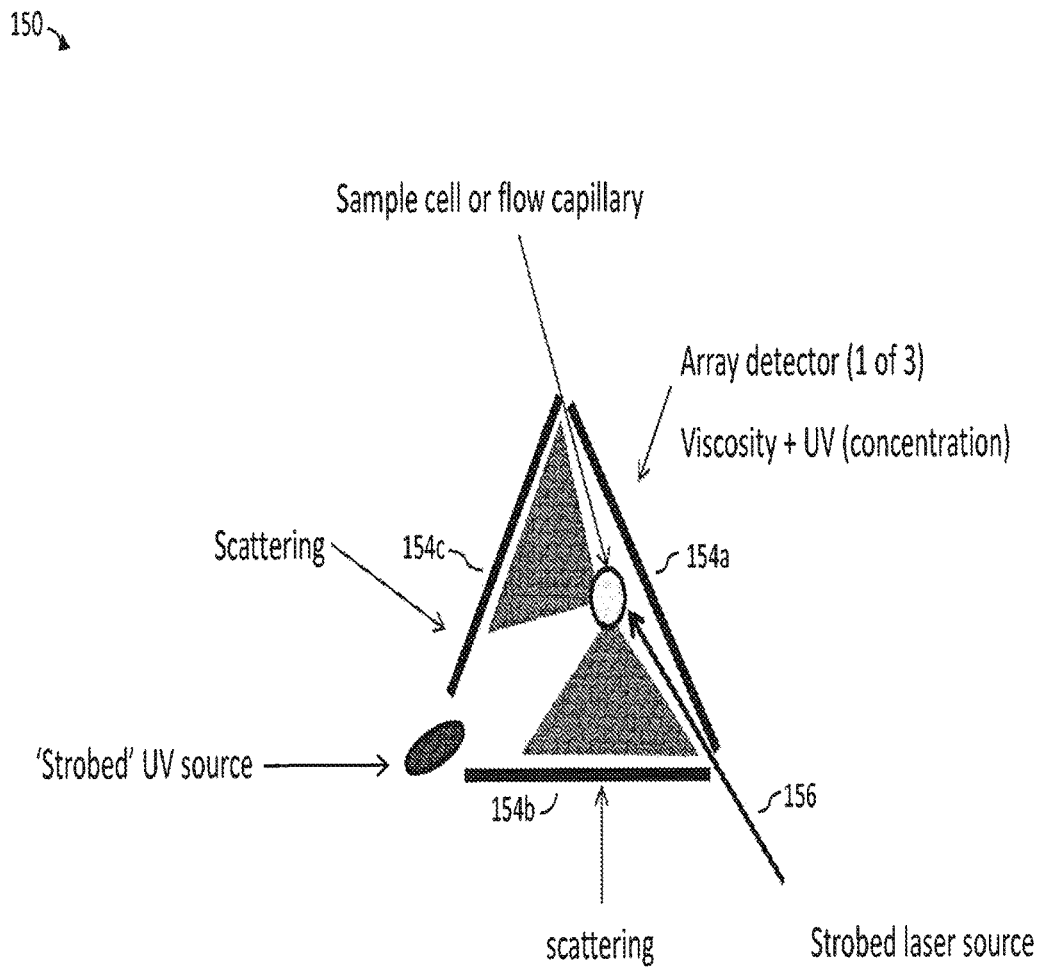
FIG. 15 is a diagrammatic top view of a three-detector sample characterization system according to the invention that measures multi-angle scattering, UV absorption, and viscosity of a sample.

Referring to FIG. 15, another embodiment of a sample characterization system 150 according to the invention includes three two-dimensional array detectors 154a, 154b, 154c, which are all oriented in the same y-direction but face inward in a spaced triangular configuration. In this case they form an isosceles triangle with openings at each vertex. Inside the triangle is a sample holder 152, which in this case is a capillary tube placed against the first two-dimensional array detector 154a.

A first illumination source, such as a laser, provides a first beam 156a that is directed through the opening between the first two-dimensional array detector 154a and the second two-dimensional array detector 154b, toward the sample holder 152. A second illumination source, such as a UV source, provides a second beam that is directed through the opening between the second two-dimensional array detector 144b and the third two-dimensional array detector 144c, toward the sample holder. The two sources are switched or strobed such that they interact separately with the sample in the sample holder during successive sampling intervals, although it may also be possible in some embodiments to perform simultaneous measurements.

This embodiment differs from that described in connection with FIG. 14 in that it detects scattering according to a somewhat different geometry and further allows for the measurement of viscosity as described in U.S. application Ser. No. 13/844,951, filed Mar. 16, 2013 (now abandoned), Ser. No. 13/773,259, filed Feb. 21, 2013, Ser. No. 13/772, 310, filed Feb. 20, 2013 (now abandoned), and Ser. No. 13/842,378, filed Mar. 15, 2013, which are all herein incorporated by reference. U.S. application Ser. Nos. 13/884,951 and 13/772,310 were abandoned in favor of U.S. application Ser. No. 14/769,149, filed Aug. 20, 2015. In addition to detecting UV transmission of the sample, therefore, the first two-dimensional array detector also detects its viscosity by measuring how long it takes for a fluid meniscus to move through the capillary tube.

Figure 16:
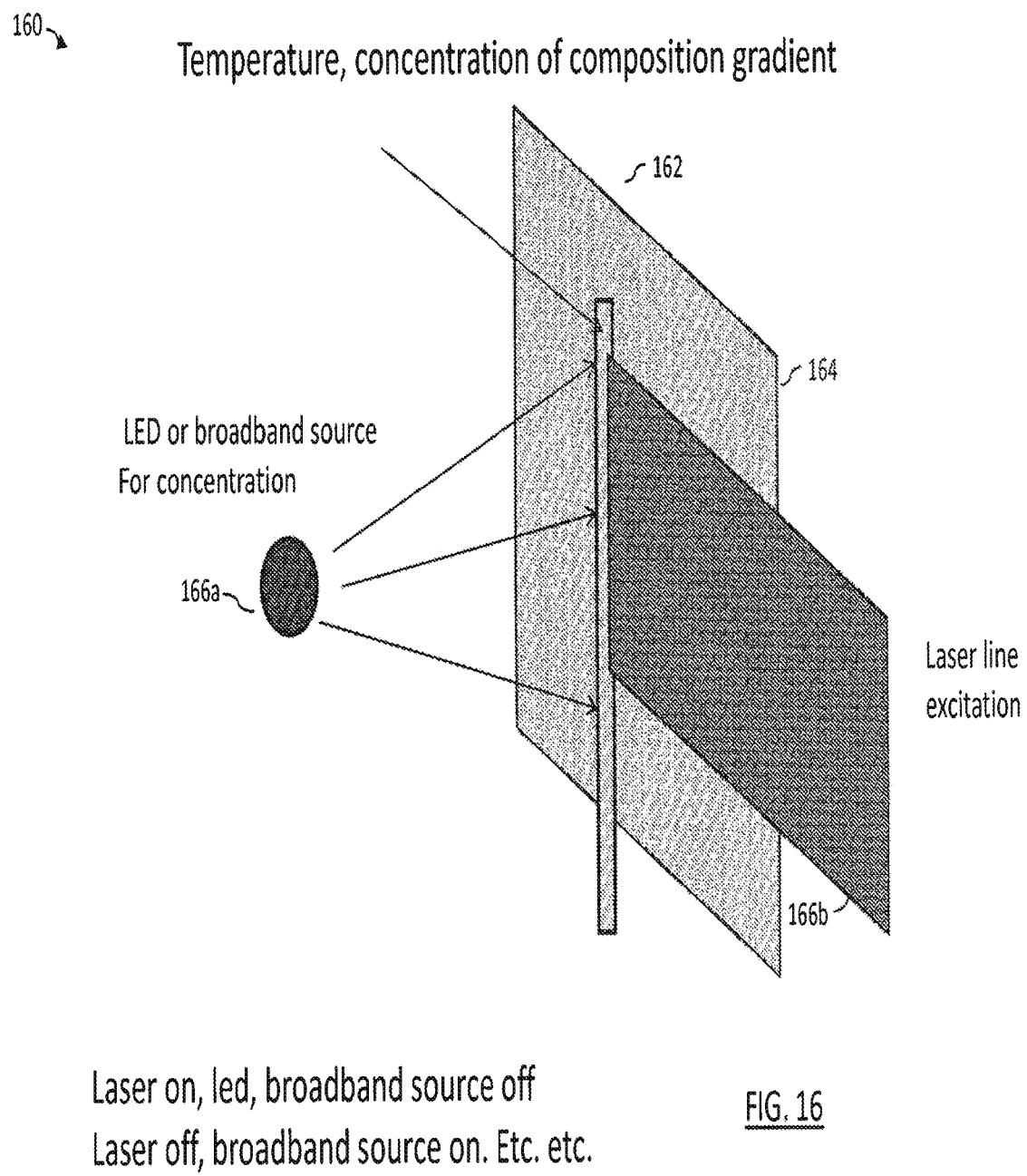
FIG. 16 is a diagrammatic perspective view of a sample characterization system according to the invention that uses an LED or broadband source and a laser line to measure absorption and scattering of a sample gradient.

Referring to FIG. 16, a further embodiment of a sample characterization system 160 according to the invention includes a two-dimensional array detector 164 and a sample holder 162, which in this case is a capillary tube placed proximate the two-dimensional array detector. A first illumination source, such as a laser equipped with a cylindrical lens, provides a first two-dimensional beam 166a that is directed toward the sample holder 162 in a first direction that can be at least generally parallel to the plane of the two-dimensional array detector and along the longitudinal axis of the capillary tube. A second illumination source, such as a UV source, provides a second beam that is directed toward the sample holder, preferably at a different angle such as at a right angle with the detector. The two sources are switched or strobed such that they interact separately with the sample in the sample holder during successive sampling intervals, although it may also be possible in some embodiments to perform simultaneous measurements.

In operation, the output beam of the first source causes scattering by the sample, which is detected by the array, and the output of the second source is partially transmitted through the sample, and detected by the array. This embodiment allows the two types of measurements to be performed over a sample in which a gradient exists.

Several embodiments have been presented above, but a number of implementations that rely on permutations of the underlying principles can be implemented. The embodiments of FIGS. 14 and 16 can be combined, for example, to measure a wide range of scattering angles for a sample in which a gradient exists. And while particular combinations of measurements have been shown, other types of measurements, such as Raman, IR, NIR, fluorescence, and reflectance measurements can be incorporated into the different embodiments and variants thereof. Each of these measurements can be produced using a particular combination of source(s), filter(s), and/or detector(s).

It should also be observed that although a lens may be used to produce the beams in each of the embodiments presented above, each of them can operate without any imaging lens. The result is that systems according to the invention can be built relatively inexpensively and without the need to align or clean imaging lenses.

The present invention has now been described in connection with a number of specific embodiments thereof. However, numerous modifications which are contemplated as falling within the scope of the present invention should now be apparent to those skilled in the art. In addition, the order of presentation of the claims should not be construed to limit the scope of any particular term in the claims.

It will be appreciated that any feature of any dependent claim could be used in combination with any number of features of other dependent claims, and in any combination of features. All numbers and combinations of dependent claims are hereby disclosed, dependent from any independent claim.

The invention claimed is:

1. An optical sample characterization method, comprising:
   supporting a sample comprising a plurality of particles in a sample holder proximate to at least one two-dimensional detector array assembly,
   illuminating the sample with an illumination beam,
   detecting an extent of deflection of the illumination beam by refraction in the illuminated sample using the two-dimensional detector array assembly,
   deriving information about refractive indices of the plurality of particles based on results of the step of detecting an extent of deflection,
   detecting one or more widths or durations of obscurations of portions of the illumination beam by the illuminated sample using the two-dimensional detector array assembly,
   deriving dimensions of the plurality of particles from the detected one or more widths or durations of obscurations of portions of the illumination beam, and
   analyzing the derived information about refractive indices to determine numbers of particles against their refractive indices.

2. The method of claim 1 wherein the illumination beam comprises a two-dimensional illumination beam.

3. The method of claim 1 wherein illuminating the sample is performed by an illumination source and a moving mirror.

4. The method of claim 1 wherein the sample holder comprises a capillary tube and wherein supporting the sample provides a flowing sample eluting from a chromatography column.

5. The method of claim 1 wherein supporting a sample comprises setting up a gradient in the sample.

6. The method of claim 1 wherein the sample holder comprises a flow cell and wherein the method comprises:
   detecting interactions between the illumination beam and particles in the illuminated sample using the two-dimensional detector array assembly as the particles pass through the illumination beam, and
   deriving information about the particles based on results of the detecting interactions.

7. The method of claim 6 wherein detecting interactions comprises detecting obscurations of portions of the illumination beam and deflections of portions of the illumination beam due to refraction, and deriving information about the particles comprises determining a spatial dimension of a particle and/or a refractive index of a particle.

8. The method of claim 6 wherein the illumination beam comprises a two-dimensional illumination beam.

9. An apparatus that detects properties of a sample comprising a plurality of particles, comprising:
   a sample holder for holding the sample,
   a first illumination source configured to illuminate the sample in the sample holder with a first illumination beam, the sample holder and first illumination source configured such that the first illumination beam is deflected by an amount related to refractive indices of the plurality of particles,
   a first two-dimensional array detector positioned proximate to the sample holder, opposite the sample holder from the first illumination source and arranged to detect an extent of deflection of the first illumination beam, and configured to detect one or more widths or durations of obscurations of the first illumination beam by a particle in the sample, and
   image analysis logic configured to calculate sample refractive indices of the plurality of particles from the extent of deflection of the beam detected by the first two-dimensional array detector, configured to calculate sample dimensions of the plurality of particles from the detected one or more widths or durations of obscurations of the first illumination beam by the first two-dimensional array detector, and configured to analyze the sample refractive indices to determine numbers of particles against their refractive indices.

10. The apparatus of claim 9 wherein the first illumination source is configured to illuminate different parts of the sample in the sample holder.

11. The apparatus of claim 10 wherein the first illumination source comprises a moving mirror.

12. The apparatus of claim 9 comprising a second two-dimensional array detector proximate to the sample holder and positioned at an angle to the first two-dimensional array detector.

13. The apparatus of claim 9 wherein the apparatus comprises a second illumination source configured to illuminate the sample in the sample holder with a second illumination beam, wherein the second illumination source and the first illumination source are not identical.

14. The apparatus of claim 9 wherein the image analysis logic is configured to derive information about the particles in the sample based on results of detecting interactions and deriving information about the particles comprises determining a spatial dimension of a particle and/or a refractive index of a particle.

15. The apparatus of claim 9 wherein the sample holder comprises a capillary tube and wherein the apparatus comprises a chromatography column upstream of the sample holder.

16. The apparatus of claim 9 wherein the apparatus does not comprise an imaging lens.

* * * * *